United States Patent [19]

Regnier et al.

[11] Patent Number: 5,225,411

[45] Date of Patent: Jul. 6, 1993

[54] DISUBSTITUTED POLYMETHYLENEIMINES

[75] Inventors: Gilbert Regnier, Chatenay Malabry; Alain Dhainaut, Chatou; Ghanem Atassi, Saint Cloud; Alain Pierre, Marly le Roi; Stéphane Leonce, Versailles, all of France

[73] Assignee: Adir et Compagnie, Courbevoie, France

[21] Appl. No.: 728,137

[22] Filed: Jul. 10, 1991

[30] Foreign Application Priority Data

Jul. 11, 1990 [FR] France .................. 90 08817

[51] Int. Cl.⁵ .................. C07D 401/04; A61K 31/53
[52] U.S. Cl. .................. 514/245; 514/212; 540/598; 544/198
[58] Field of Search .................. 540/598; 544/198; 514/245, 212

[56] References Cited

FOREIGN PATENT DOCUMENTS 0090733 10/1983 European Pat. Off. .

Primary Examiner—John M. Ford
Attorney, Agent, or Firm—Gordon W. Hueschen

[57] ABSTRACT

The compounds are 2,4-(optionally substituted amino)-6-substituted s.triazines, useful for suppressing the resistance of tumour cells to anti-cancer agents and for suppressing the resistance of parasites to anti-parasitic agents.

A compound disclosed is 1-[4,6-bis(allylamino)-2-s-triazinyl]-4-[2,2-bis(p.fluorophenyl)ethylamino]piperidine.

5 Claims, No Drawings

DISUBSTITUTED POLYMETHYLENEIMINES

The present invention relates to disubstituted polymethyleneimines of formula I:

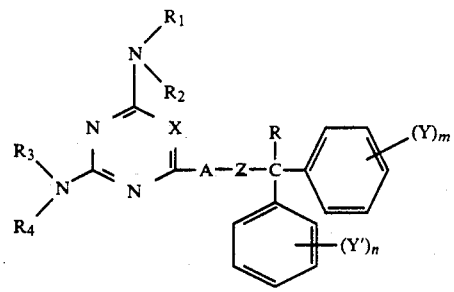

in which:

a) X represents a CH group or a nitrogen atom;

b) A represents a polymethyleneimine group of the formula:

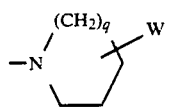

in which:
W is a hetero atom:oxygen or sulfur or is a radical NR, in which R' represents a hydrogen atom or an alkyl or alkenyl radical each having up to 5 carbon atoms, and
q is an integer from 1 to 3;

c) $R_1$, $R_2$, $R_3$ and $R_4$, which are the same or different, each represents:
a hydrogen atom,
a straight-chain or branched alkyl radical containing from 1 to 6 carbon atoms that is optionally substituted by a halogen atom, by one or more hydroxy radicals or by an aminated radical: —$N(R_5 R_6)$ in which $R_5$ and $R_6$, which are the same or different, each represents a hydrogen atom or a straight-chain or branched alkyl radical containing from 1 to 6 carbon atoms or
$R_5$ and $R_6$, together with the nitrogen atom to which they are attached, form a heterocycle containing from 4 to 6 carbon atoms and, optionally, an additional hetero atom: oxygen or sulfur;
an alkenyl or alkynyl radical each containing from 2 to 6 carbon atoms;
or
a cycloalkyl radical containing from 3 to 6 carbon atoms;
or
each of the pairs $R_1$, $R_2$ and/or $R_3$, $R_4$, together with the nitrogen atom to which they are attached, form a heterocycle containing from 4 to 6 carbon atoms and, optionally, an additional hetero atom: oxygen or sulfur;

d) Z represents a straight-chain or branched hydrocarbon radical containing from 1 to 5 carbon atoms;

e) R represents a hydrogen atom, a straight-chain or branched alkyl radical containing from 1 to 5 carbon atoms, a straight-chain or branched alkenyl radical containing from 2 to 5 carbon atoms, or a phenyl radical optionally substituted by $(Y)_m$ or $(Y')_n$;

f) Y and Y', which are the same or different, each represents a hydrogen or halogen atom, a trifluoromethyl radical, or an alkyl or alkoxy radical each containing from 1 to 5 carbon atoms;

g) m and n, which are the same or different, each represents an integer 1 or 2.

The prior art is illustrated especially by French Patent No. 2 524 467 which relates to polymethyleneimines of the formula:

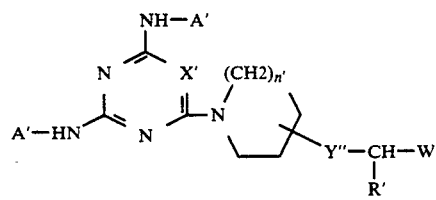

in which:

A' is a $C_3C_5$ alkenyl radical optionally substituted by one or more OH groups;

X' represents CH or N;

n' represents zero, one or two;

Y" represents O or N—$R'_1$ [$R'_1$ being hydrogen, ($C_1$-$C_5$)-alkyl or -hydroxyalkyl, ($C_2$-$C_5$)alkenyl, or ($C_3$-$C_7$) -cycloalkyl or -cycloalkenyl];

R' is hydrogen, ($C_1$-$C_5$)alkyl, ($C_5$-$C_7$)cycloalkyl or optionally substituted phenyl, and W is especially ($C_1$-$C_5$)alkyl, ($C_2$-$C_5$)alkenyl, phenyl, naphthyl, benzofuranyl, benzothienyl, benzodioxolyl, benzodioxanyl, benzodioxinyl, $\Delta^3$-chromenyl, thiochromenyl or chromanyl;

which polymethyleneimines promote the uptake of oxygen and can therefore be used in the treatment of cerebral decline.

Significant structural modifications have resulted in the compounds of formula I of the present invention, which have a particularly valuable pharmacological and therapeutic activity totally different from that of similar compounds known in the art, as demonstrated by the pharmacological study described in Example 26.

The presents invention also relates to a process for the preparation of compounds of the general formula I which is characterised in that:

either a polymethyleneimine of the general formula II:

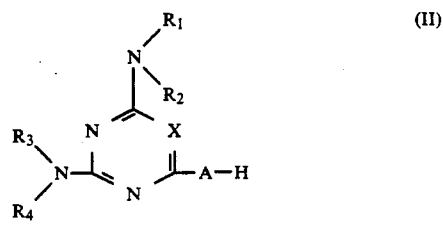

in which X, A, $R_1$, $R_2$, $R_3$ and $R_4$ are as defined hereinbefore, is condensed with a compound of the general formula III:

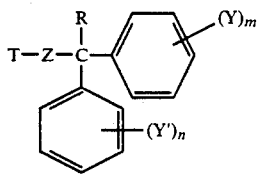
(III)

in which Z, R, Y, Y', m and n are as defined hereinbefore and T represents a halogen atoms such as, for example, a chlorine or bromine atom, or a tosyloxy radical, or a halogenated compound of the general formula IV:

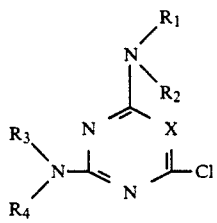
(IV)

in which X, $R_1$, $R_2$, $R_3$ and $R_4$ are as defined hereinbefore, is condensed with a polymethyleneimine of the general formula V:

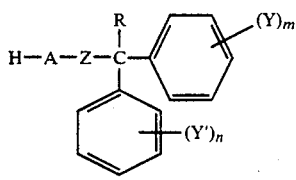
(V)

in which A, Z, R, Y, Y', m and n are as defined hereinbefore.

The condensation of compounds II and III is carried out preferably in a solvent selected from alcohols that contain 4 or 5 carbon atoms, dimethylformamide, dimethylacetamide, acetonitrile and tetrahydrofuran.

It is advantageous to carry out the condensation at a temperature of from 80° to 120° C. in the presence of an acceptor for the acid formed during the course of the reaction. That acceptor can be selected from alkali metal carbonates, such as potassium carbonate, triethylamine and an excess of the compound II used for the condensation.

On the other hand, when W represents an oxygen or sulphur atom (hence BH=OH or SH), it is advantageous to employ sodium hydride in order to introduce sodium into compound II beforehand.

The condensation of compounds IV and V is carried out especially advantageously in a solvent selected from alcohols containing 4 or 5 carbon atoms, such as butanol or pentanol, and aliphatic amides, such as dimethylformamide or dimethylacetamide. It is recommended that the reaction be carried out at a temperature of from 120° to 15° C. in the presence of an acceptor for the hydracid formed during the course of the reaction. That acceptor may be selected from alkali metal carbonates, such as potassium carbonate, triethylamine and an excess of the compound V employed for the condensation. When B represents an oxygen or sulfur atom (hence BH=OH or SH), it is advantageous to employ sodium hydride in order to introduce sodium into compound V.

The present invention also relates to a process for the preparation of compounds I in which W represents the radical NR', that is to say more particularly compounds of the general formula I':

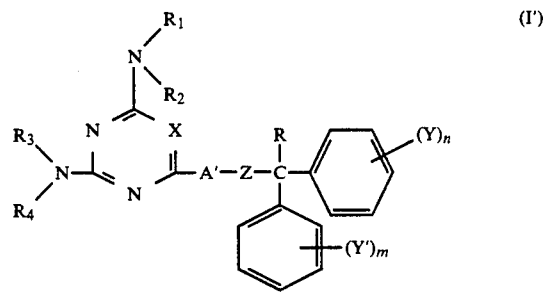
(I')

in which X, Z, R, $R_1$, $R_2$, $R_3$, $R_4$, Y, Y', m and n are as defined hereinbefore and A' represents a polymethyleneimine group of formula:

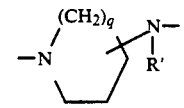

in which q and R' are as defined hereinbefore,
which process is charcterised in that a mixture of:
a ketone of the general formula VI:

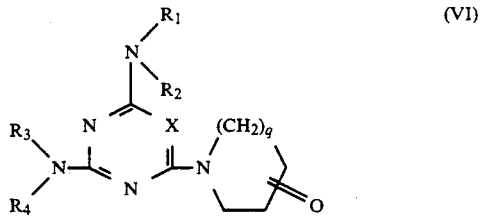
(VI)

in which X, $R_1$, $R_2$, $R_3$, $R_4$ and q are as defined hereinbefore, before,
and an amine of the general formula VII:

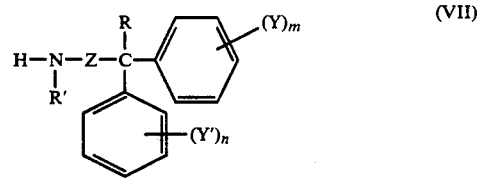
(VII)

in which R', Z, R, Y, Y', m, and n are as defined hereinbefore, is treated with sodium cyanoborohydride.

It is especially advantageous to carry out the reaction in a suitable solvent, such as a low-molecular-weight alcohol such as, for example, methanol or ethanol, or tetrahydrofuran, at a temperature of from 20° to 25° C. and a pH of approximately 6.

The starting materials used in the processes described above are either known compounds or compounds prepared from known substances in accordance with processes described for preparing similar compounds as indicated in the following Examples.

The compounds of the general formula I can be converted into addition salts with acids, the salts also as such forming part of the invention. There may be mentioned as acids that can be used for the formation of such salts, for example in the mineral series hydrochloric, hydrobromic, sulphuric, nitric and phosphoric acids, and in the organic series acetic, propionic, maleic, fumaric, tartaric, oxalic, benzoic, methanesulphonic and isethionic acids.

Furthermore, when Z is a branched chain and/or Y and Y' are different from one another and do not represent a hydrogen atom, the compounds (I) may be in the form of diastereoisomers or enantiomers which, as such, also form part of the invention.

The new compounds (I) can be purified by physical methods, such as crystallisation of the bases, chromatography (especially flash chromatrography on 35–70μ silica, under a pressure of 0.5 to 1 atmosphere of nitrogen, using $CH_2Cl_2$/methanol or ethyl acetate as eluant system), or by chemical methods, such as the formation of addition salts with acids and decomposition of those salts using alkaline agents.

The compounds of the general formula I and the physiologically tolerable addition salts thereof have valuable pharmacological and therapeutic properties, enabling them to be used to suppress the resistance of tumour cells to anti-cancer agents.

The present invention also relates to pharmaceutical compositions containing as active ingredient a compound of the general formula I or a physiologically tolerable salt thereof, in association or admixture with an appropriate pharmaceutical excipient.

The pharmaceutical compositions so-obtained are generally in dosage form. They may, for example, be in the form of tablets, dragees, soft gelatin capsules, suppositories, or injectable or drinkable solutions, and be administered orally, rectally or parenterally.

The posology can vary especially in accordance with the age and weight of the patient, the administration route, the nature of the illness, and associated treatments, and ranges from 0.1 to 7 g per dose.

The following Examples illustrate the invention. Melting points are determined using a capillary tube (cap.) or a Kofler hot plate (K).

EXAMPLE 1

1-[4,6-bis(allylamino)-2-s-triazinyl]-4-[2,2-bis(p-fluorophenyl)ethylamino]piperidine.

A) First Method 17 g of 2,2-bis(p-fluorophenyl)ethylamine (b.p./$7_{mm}$=158°–160° C.) and then 23.7 g of 1-[4,6 bis-(allylamino)-2-triazinyl]4-piperidone hydrochloride, melting (cap.) at 219°–222° C., are added in succession, at a temperature of 15° to 20° C., to a solution of 4.6 g of sodium cyanoborohydride in 150 ml of methanol containing 20 g of a 3Å molecular sieve.

The pH is adjusted to 6 by the addition of methanolic hydrogen chloride and the mixture is stirred for 24 hours at room temperature.

At the end of that period, the insoluble material is filtered off and the filtrate is evaporated under reduced pressure.

The residue is taken up in ether, washed with water and then with a 10% $NaHCO_3$ solution.

Drying is carried out over $MgSO_4$ and, after evaporation, the residue is chromatographed on $SiO_2$ using $CH_3COOC_2H_5$ as eluant. After evaporation of the eluates, the crystalline residue is recrystallised from 90% ethanol. 5.3 g of monohydrate melting (cap.) at 66°–68° C. are obtained.

The 1-[4,6-bis(allylamino)-2-triazinyl)-4-piperidone hydrochloride used as starting material was prepared by condensing 4,6-diallylamino-2-chlorotriazine with 4,4-diethoxypiperidine, then hydrolysing the resulting diethoxylated compound using dilute HCl to obtain the corresponding piperidone.

B) Second Method

A solution of 2.9 g of 4,6-bis(allylamino)-2-(4-aminopiperidino)-1,3,5-triazine, melting (cap.) at 120° C., and 3 g of 2,2-bis(p-fluorophenyl)-1-bromoethane in 50 ml of dimethylformamide is heated for 8 hours at 120° C. in the presence of 1.2 g of triethylamine.

When the reaction is complete, the solvent is evaporated off under reduced pressure and the residue is taken up in ether and then washed with water. After removal of the ether by evaporation, the oily residue is chromatographed on $SiO_2$ using $CH_3COOC_2H_5$ as eluant.

Evaporation of the eluates leaves a crystalline residue which is crystallised from 90% ethanol. 1.9 g of monohydrate crystals melting (cap.) at 66°–68° C. are obtained.

The 4,6-bis(allylamino)-2-(4-aminopiperidino)-1,3,5-triazine used as starting material was prepared by condensing 4-acetamidopiperidine with 4,6-bis(allylamino)-2-chlorotriazine in dimethylformamide, followed by hydrolysis of the resulting compound with a solution of sodium hydroxide in ethanol.

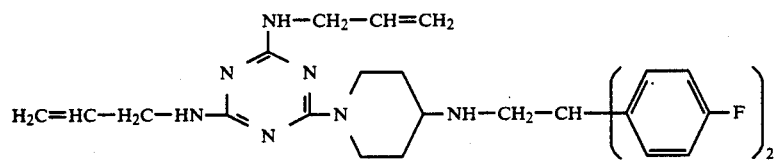

EXAMPLE 2

1-[4,6-bis(allylamino)-2-s-triazinyl]-4-(3,3-diphenylpropylthio)piperidine.

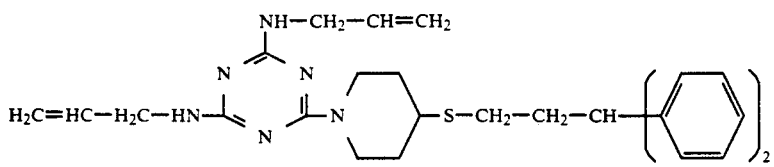

A solution of 3.6 g of 4,6-bis(allylamino)-2-chlorotriazine and 5 g of 4-(3,3-diphenylpropylthio)piperidine in 100 ml of butanol is heated at reflux for 10 hours in the presence of 4.4 g of $K_2CO_3$. When the reaction is complete, the salt is filtered off and the solvent is evaporated off under reduced pressure. The residue is taken up in ether. 9 g of oil are obtained from which the fumarate, prepared in ethanol, yields 7.8 g of crystals melting (K) at 168° C.

The piperidine used as starting material, the fumarate of which melts (K) at 160° C., was prepared by hydrolysing the corresponding N-ethoxycarbonyl compound with $(CH_3)_3SiCl$.

EXAMPLE 3

4-[4,6-bis(allylamino)-2-s-triazinyl]amino-1-(2,2diphenylethyl)piperidine

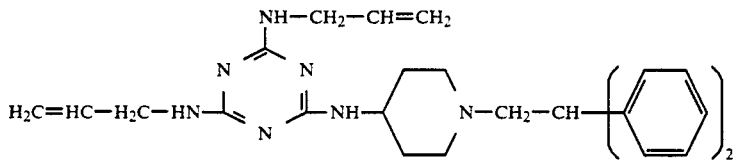

A solution of 2.3 g of 4,6-diallylamino-2-chloro-1,3,5-triazine and 2.8 g of 4-amino-1-(2,2-diphenylethyl)-piperidine is heated at reflux for 10 hours in 50 ml of butanol in the presence of 1.4 ml of triethylamine. When the reaction is complete, the butanol is evaporated off under reduced pressure and the residue is taken up in ether.

The ethereal solution is washed with water and then the ether is evaporated off. The oily residue is purified by chromatography on $SiO_2$ using $CH_3COOC_2H_5$ as eluant.

Evaporation of the eluates yields 2.6 g of a product in resinous form.

The 4-amino-1-(2,2-diphenylethyl)piperidine used as starting material, melting point (cap.): 41°–45° C., was prepared by reductive alkylation, with $NaBH_3CN$ in methanol, of a mixture of diphenylacetaldehyde and 4-acetamidopiperidine, followed by hydrolysis of the resulting 1-diphenylethyl-4-acetamidopiperidine with 4N HCl.

EXAMPLE 4

1-[4,6-bis(allylamino)-2-s-triazinyl)-4-[N-(2,2-diphenylethyl)-N-methylamino]piperidine.

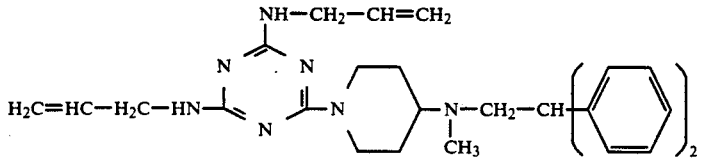

A solution of 2.3 g of 4,6-diallylamino-2-chloro-1,3,5-triazine, melting (cap.) at 206°–208° C., and 3 g of 4-[N(2,2-diphenylethyl)-N-methylamino]piperidine in 50 ml of dimethylformamide is heated for 8 hours at 130° C. in the presence of 1.4 g of $K_2CO_3$. When the reaction is complete, the salt is filtered off and the solvent is evaporated off under reduced pressure.

The residue is chromatographed on $SiO_2$ using $CH_2Cl_2/CH_3OH$ (95:5) as eluant.

3.2 g of an oily product are obtained, the difumarate of which melts (cap.) at 172°–176° C.

The piperidine (oil) used as starting material was prepared by reductive alkylation, using $NaBH_3CN$ in methanol, of 1-acetyl-4-piperidone with N-(2,2-diphenylethyl)-N-methylamine [m.p. (cap.) of the oxalate=215° C.] followed by alkaline hydrolysis with $NaOH/C_2H_5OH$.

The 1-[4,6-bis(allylamino)-2-s-triazinyl]-4-[N-(diphenylethyl)-N-methylamino]piperidine was similarly prepared in accordance with the process described in method B of Example 1).

EXAMPLES 5 TO 28

The following compounds were prepared using one or more of the preparation processes described in Examples 1 to 4:

5) 1-[4,6-bis(allylamino)-2-s-triazinyl]-4-(2,2-diphenylethylamino)piperidine, m.p. (cap.): 69°–72° C.

6) 1-[4,6-bis(allylamino)-2-s-triazinyl]-4-(3,3-diphenylpropylamino)-piperidine, m.p. (cap.): 88°–92° C.

7) 1-(4-propylamino-6-allylamino-2-s-triazinyl)-4-(2,2-diphenylethylamino)piperidine, m.p. (cap.): 56°–58° C.

8) 1-(4-propylamino-6-allylamino-2-s-triazinyl)-4-(3,3diphenylpropylamino)piperidine, m.p. (cap.): 78°–83° C.

9) 1-(bis-2,4-allylamino-6-pyrimidinyl)-4-(3,3-diphenylpropylamino)piperidine, m.p. (cap.) of the fumarate: 209°–211° C.

10) 1-[4,6-bis(allylamino)-2-s-triazinyl]-4-[2-(3,5-dimethoxyphenyl)-2-(2-methylphenyl)ethylamino]piperidine, m.p. (cap.) of the difumarate: 178°–184° C.

11) 4-(4-allylamino-6-propylamino-2-s-triazinylamino)-1-(2,2-diphenylethyl)piperidine.
12) 1-[4,6-bis(allylamino)-2-s-triazinyl]-4-[3,3-bis( 3,4-dimethoxyphenyl)propylamino]piperidine, m.p. (cap.) of the fumarate: 180°-182° C.
13) 1-[4,6-bis(diallylamino)-2-s-triazinyl]-4-(2,2-diphenylethylamino)piperidine, m.p. (cap.) of the fumarate: 206°-210° C.
14) 4-[4,6-bis(allylamino)-2-s-triazinylthio]-1-(2,2-diphenylethyl)piperidine.
15) 4-[4,6-bis(allylamino)-2-s-triazinyloxy]-1-(2,2-diphenylethyl)piperidine.
16) 1-[4,6-bis(allylamino)-2-s-triazinyl]-4-(3,3-diphenylpropoxy)piperidine.
17) 1-[4,6-bis(allylamino)-2-s-triazinyl]-4-(2,2,2-triphenylethylamino)piperidine.
18) 1-(4-allylamino-6-amino-2-s-triazinyl)-4-(2,2-diphenylethylamino)piperidine.
19) 1-[4,6-bis(3,3-dimethylallylamino)-2-s-triazinyl]-4-(2,2-diphenylethylamino)piperidine.
20) 1-[4,6-bis(3-methylallylamino)-2-s-triazinyl]-4-(2,2-diphenylethylamino)piperidine.
21) 1-[4,6-bis(2,2-hydroxyethylamino)-2-s-triazinyl]-4-(2,2-diphenylethylamino)piperidine.
22) 1-[4,6-bis(3-chloroallylamino)-2-s-triazinyl]-4-(2,2-diphenylethylamino)piperidine.
23) 1-[4,6-bis(cyclopropylamino)-2-s-triazinyl]-4-(2,2-diphenylethylamino)piperidine.
24) 1-[4,6-bis(2,2-dimethylaminoethylamino)-2-s-triazinyl]-4-(2,2-diphenylethylamino)piperidine.
25) 1-[4,6-bis(N-allyl-N-methylamino)-2-s-triazinyl]-4-(2,2-diphenylethylamino)piperidine.
26) 1-[4,6-bis(diallylamino)-2-s-triazinyl]-4-(2,2-diphenylethylamino)piperidine, m.p. (cap.) of the fumarate : 206°-210° C.
27) 1-[4,6-bis(allylamino)-2-s-triazinyl]-4-(2,2,2-triphenylethylamino)piperidine, m.p. (cap.): 35°-136° C.
28) 1-[4,6-bis(allylamino)-2-s-triazinyl]-4-[2,2-bis(2,6-dimethylphenylethylamino]piperidine, m.p. (cap.) of the fumarate: 205°-207° C.

EXAMPLE 29

Pharmacological Study

Resistance to anti-cancer agents is a major obstacle to the effectiveness of antitumour drugs. When tumour cells are exposed in vitro or in vivo to an anti-cancer agent they become resistant to varying degrees to those compounds.

Numerous mechanisms have been described by which a cell acquires resistance to anti-cancer agents. Of the different types of resistance, "Multidrug Resistance" (MDR) is of particular interest. The phenomenon of resistance is as a result of the action of an inducible membrane protein, gP 170, the role of which is to increase the efflux of the cytotoxic agent, thus reducing its intracellular concentration, resulting in the loss in sensitivity of those cells to the drug.

Agents, used in other pathologies, are known for the partial or complete reversal of that resistance (Int. J. Cancer Res. (1988) +9 pp 285-296; I.N.C.I. (1989) 81 pp 907-910; Trends Pharmacol. Sci. (1989) 9 pp 54-58; Annu. Rev. Biochem. (1989) 58 pp 137-171.

When the modulating agent is added at the same time as the cytotoxic agent it reduces or completely suppresses MDR-type resistance. Certain agents used for the treatment of other diseases, such as amiodarone, verapamil or cyclosporine, have been used clinically to overcome that resistance, but their intrinsic pharmacological properties (hypotensive agents, or immunosuppressors), which are often undesirable when treating cancer, and their toxicity limits their use considerably.

Furthermore, the mechanism of resistance to chloroquine developed by Plasmodium falciparum is similar. Verapamil restores the sensitivity of a resistant line, which demonstrates the potential value of compounds that reverse the MDR phenotype of tumour cells for use in parasitology. (Science (1987), 238pp 1283-1285; Science (1987), 235, pp 899-901).

The tests described hereinafter show that the compounds of the present invention reverse acquired resistance to various medicaments.

A) Evaluation of the ncrease In Cytotoxicity of Adriamycin on the Line P 388/ADR-10 in Vitro In this study, the cytotoxicity of adriamycin was measured in the absence and in the presence of the reversing compound. For this assay, the murine leukaemia P 388/ADR 10 was used, the resistance of which had been induced by adriamycin. Its factor of resistance is 260 in relation to the sensitive line (mean resistance).

The cells are cultivated in a complete culture medium (RPMI 1640), containing 10% foetal calf serum, 2 nM glutamine, 50 IU/ml penioillin, 50 µg/ml streptomycin, 10 mM Hepes and 20 nM beta-mercaptoethanol.

The cells are distributed on microplates and exposed to 9 different concentrations of adriamycin.

The compounds tested for their capacity to reverse MDR are added at the same time as the cytotoxic agent. The cells are then incubated for 48 hours.

The number of viable cells is then quantified by a colorimetric assay, the Microculture Tetrazolium Assay (Cancer Res. (1987), 47, pp 936-942).

The results are expressed as IC$_{50}$, the concentration of cytotoxic agent that inhibits the proliferation of the control cells by 50%. The results are expressed as Reversion Factor (RF).

$$RF = \frac{IC_{50} \text{ cytotoxic agent only}}{IC_{50} \text{ cytotoxic agent in the presence of the reversing compound}}$$

Table I gives the reversion factor values obtained with different compounds of formula I and with the reference compounds, and demonstrates the very valuable activity of the compounds of formula I.

Regarding reserpine (one of the reference compounds), that compound has a very good activity in vitro, but it cannot be used in vivo in view of its high degree of toxicity.

TABLE I

| COMPOUNDS | 2.5 µM | 5 µM | 10 µM |
|---|---|---|---|
| REFERENCE COMPOUNDS | | | |
| PHENOTHIAZINE | 9.4 | 23.1 | — |
| PROGESTERONE | — | 1.7 | 2.5 |
| FLUNARIZINE | — | — | 25 |
| QUINIDINE | — | 6 | 17.4 |
| QUININE | — | — | 14.5 |
| VERAPAMIL | 13.5 | 36.3 | 67.2 |
| AMIODARONE | 37.7 | 104.7 | TOX |
| RESERPINE | — | 215.5 | 189 |
| CYCLOSPORINE | 149.4 | TOX | TOX |
| COMPOUNDS OF THE EXAMPLE | | | |
| EXAMPLE 1 | 110.8 | 244.4 | 170.7 |
| EXAMPLE 2 | 15.4 | 65.1 | 86.4 |
| EXAMPLE 3 | 39 | 70 | 134.8 |
| EXAMPLE 4 | 34.7 | 32.3 | 171.1 |

TABLE I-continued

| COMPOUNDS | 2.5 μM | 5 μM | 10 μM |
|---|---|---|---|
| EXAMPLE 5 | 100 | 189 | 277.4 |
| EXAMPLE 6 | 54.4 | TOX | TOX |
| EXAMPLE 7 | 102.8 | 135.6 | TOX |
| EXAMPLE 8 | 75.9 | TOX | TOX |
| EXAMPLE 9 | 80.4 | TOX | TOX |
| EXAMPLE 10 | 125.1 | 75.3 | TOX |
| EXAMPLE 11 | 87 | 65.2 | TOX |
| EXAMPLE 12 | 1.4 | 8 | TOX |

Evaluation of the Increase in the Cytotoxicity of Actinomycin D on the Chinese Hamster Pulmonary Line DC-3F/AD The protocol used for this study is identical to that used for the assay described in Example 1, but the culture medium did not contain beta-mercaptoethanol and the cells were incubated for 4 days instead of 48 hours. The cytotoxic agent used was actinomycin D.

Line DC-3F/AD is an extremely resistant line. Its resistance factor is higher than 10,000.

The results of this study are given in Table II:

The results of Table II show that the compounds of formula I significantly reduce or suppress the resistance to the cytotoxic agent.

TABLE II

| COMPOUNDS | 2.5 μM | 5 μM | 10 μM | 20 μM |
|---|---|---|---|---|
| REFERENCE COMPOUNDS | | | | |
| PHENOTHIAZINE | — | <12 | <12 | <12 |
| CHLOROPROMAZINE | — | <13 | <12 | <13 |
| YOHIMINE | — | <12 | <12 | <12 |
| NIFEDIPINE | — | <11 | TOX | TOX |
| PROGESTERONE | — | <10 | <10 | 13 |
| QUININE | — | <10 | <10 | <11 |
| DILTIAZEM | — | <11 | <10 | <11 |
| FLUNARIZINE | — | <13 | 16 | TOX |
| DIPYRIDAMOLE | — | <12 | <11 | <12 |
| QUINIDINE | — | <12 | <12 | <12 |
| QUINACRINE | — | <13 | <12 | TOX |
| TRIFLUOPERAZINE | — | <12 | 38 | TOX |
| VERAPAMIL | — | <13 | 31 | 117 |
| AMIODARONE | — | 298 | 388 | TOX |
| PIMOZIDE | <10 | 28 | 78 | TOX |
| RESERPINE | 258 | 1085 | 1649 | 2024 |
| CYCLOSPORINE | <11 | <11 | 11 | 10 |
| COMPOUNDS OF THE EXAMPLES | | | | |
| EXAMPLE 1 | 171 | 905 | 2575 | TOX |
| EXAMPLE 2 | — | 17 | 171 | — |
| EXAMPLE 3 | 38 | 104 | 240 | — |
| EXAMPLE 4 | — | 218 | 1256 | — |
| EXAMPLE 5 | — | 658 | 1504 | TOX |
| EXAMPLE 6 | <16.5 | 220 | TOX | TOX |
| EXAMPLE 7 | — | 992 | 2339 | — |
| EXAMPLE 8 | 16.5 | TOX | TOX | TOX |
| EXAMPLE 9 | 94 | 472 | TOX | — |
| EXAMPLE 10 | 259 | 1347 | TOX | — |
| EXAMPLE 11 | — | 281 | 926 | — |
| EXAMPLE 12 | — | <16.5 | <16.5 | — |

C) Flow Cytometry

Certain anti-cancer compounds, such as adriamycin (ADR), exhibit the property of being fluorescent after excitation by a light source of known wavelength.

By measuring that fluorescence it is possible to obtain a relative measurement of the intracellular concentration of ADR. Flow cytometry (FCM) is a preferred method of carrying out this kind of measurement and thus quickly determining if certain active compounds cause an increase in the intracellular concentration of adriamycin.

The cells (500×10³) per ml were simultaneously exposed to adriamycin at a fixed concentration (50 μM) and to the test compounds at concentrations of 2.5, 10 and 20 μM. After 5 hours' incubation, the intracellular uptake of adriamycin was evaluated by FCM.

The analyses were carried out on flow cytometer ATC 3000 (Bruker - France) fitted with a 2025 argon laser (Spectra-Physics-France ®) optimised at 488 nm for a power of 600 mW.

The analysis of each of the samples was carried out on a total of 10,000 cells at a speed of 1000 cells/sec.

The results were presented in the form of linear histograms of the intracellular ADR fluorescence.

Expression of the Results

For each of the histograms, the channel mean fluorescence was determined by the apparatus information system. For all experiments:

A negative control (cells without ADR) fixed the autofluorescence threshold.

A positive control (cells with ADR) determined the MEAN value=MN1.

The "test" tubes (cells with ADR and with compound) were used to determine, for each of the compounds and at each of the concentrations, the MEAN values=MN2.

The results are expressed in the form of variations from the mean fluorescence obtained for each of the "test" tubes (MN2) in relation to the mean fluorescence obtained with the positive control (MN1) : VAR-MEAN=MN2 −MN1. The parameter expressed is thus the increase in the fluorescence of adriamycin in the presence of the tested compounds.

Table III gives the increase in fluorescence of ADR obtained with different compounds on the line DC-3F/AD and Table IV on the line P 388/ADR 10.

TABLE III

| COMPOUNDS | 2 μM | 5 μM | 10 μM | 20 μM |
|---|---|---|---|---|
| REFERENCE COMPOUNDS | | | | |
| VERAPAMIL | 2.00 | 2.60 | 7.55 | 11.45 |
| AMIODARONE | 8.80 | 16.65 | 21.55 | 26.35 |
| PIMOZIDE | 5.85 | 8.85 | 15.65 | 21.60 |
| RESERPINE | 26.18 | 29.43 | 31.73 | 29.95 |
| CYCLOSPORINE | 1.90 | 3.20 | 8.05 | 15.10 |
| QUINACRINE | 2.00 | 10.5 | 19.1 | 25.8 |
| TRIFLUOPERAZINE | 0.00 | 0.00 | 4.10 | 13.40 |
| COMPOUNDS OF THE EXAMPLES | | | | |
| EXAMPLE 1 | 18.27 | 26.13 | 35.57 | 43.63 |
| EXAMPLE 2 | 0.2 | 10.4 | 25.1 | 35.0 |
| EXAMPLE 3 | 8.0 | 19.9 | 21.6 | 19.3 |
| EXAMPLE 4 | 12.3 | 24.1 | 41.9 | 49.0 |
| EXAMPLE 5 | 15.5 | 31.3 | 34.65 | 37.9 |
| EXAMPLE 6 | 3.9 | 21.5 | 29.75 | TOX |
| EXAMPLE 7 | 14.47 | 26.0 | 34.17 | 36.63 |
| EXAMPLE 8 | 4.5 | 17.85 | 27.15 | TOX |
| EXAMPLE 9 | 7.2 | 15.1 | 16.3 | 26.2 |
| EXAMPLE 10 | 14.8 | 24.7 | 26.5 | 28.2 |
| EXAMPLE 11 | 12.6 | 18.9 | 29.9 | 40.5 |
| EXAMPLE 12 | 6.1 | 3.8 | 5.5 | 9.6 |

TABLE IV

| COMPOUNDS | 2 μM | 5 μM | 10 μM | 20 μM |
|---|---|---|---|---|
| REFERENCE COMPOUNDS | | | | |

TABLE IV-continued

| COMPOUNDS | 2 μM | 5 μM | 10 μM | 20 μM |
|---|---|---|---|---|
| PHENOTHIAZINE | 0.00 | 0.00 | 0.00 | 0.00 |
| CHLOROPROMAZINE | 3.30 | 5.15 | 4.60 | 6.20 |
| YOHIMBINE | 2.30 | 0.05 | 4.70 | 3.45 |
| NIFEDIPINE | 0.00 | 0.80 | 5.95 | 3.40 |
| PROGESTERONE | 1.85 | 1.00 | 6.85 | 11.80 |
| QUININE | 4.85 | 5.40 | 12.00 | 18.90 |
| DILTIAZEM | 3.10 | 6.65 | 13.45 | 23.15 |
| FLUNARIZINE | 7.35 | 10.10 | 19.90 | 41.00 |
| DIPYRIDAMOLE | 2.35 | 7.55 | 21.75 | 40.00 |
| QUINIDINE | 6.65 | 12.80 | 22.00 | 29.90 |
| QUINACRINE | 11.83 | 15.73 | 27.73 | 52.77 |
| TRIFLUOPERAZINE | 11.45 | 14.75 | 34.55 | 51.05 |
| VERAPAMIL | 9.89 | 21.90 | 39.62 | 56.50 |
| AMIODARONE | 33.40 | 65.25 | 76.33 | 95.85 |
| PIMOZIDE | 25.60 | 49.42 | 73.13 | 73.64 |
| RESERPINE | 73.46 | 80.48 | 91.90 | 85.39 |
| CYCLOSPORINE | 79.43 | 97.63 | 96.68 | 90.27 |
| COMPOUNDS OF THE EXAMPLES | | | | |
| EXAMPLE 1 | 53.1 | 74.1 | 85.49 | 78.5 |
| EXAMPLE 3 | 29.9 | 46.2 | 66.0 | 73.1 |
| EXAMPLE 5 | 45.25 | 60.7 | 79.47 | 76.25 |
| EXAMPLE 6 | 32.9 | 60.1 | 55.8 | TOX |
| EXAMPLE 7 | 48.75 | 72.6 | 80.9 | 87.3 |
| EXAMPLE 8 | 38.9 | 60.1 | TOX | TOX |
| EXAMPLE 9 | 39.2 | 55.8 | 65.8 | TOX |
| EXAMPLE 10 | 52.0 | 75.3 | 84.0 | 78.0 |

D) In Vivo Reversion of the Acquired Resistance to Medicaments

The compound of Example 1 was tested on a tumour presenting the MDR phenotype, murine leukaemia P388/ADR. Several ratios of doses of the compound of Example 1 and adriamycin were used.

Leukaemia P388/ADR (resistant to ADR) originates from the National Cancer Institute (USA).

$10^6$ cells are implanted by the intraperitoneal route into female $B_6D_2F_1$ mice on day 0 and treatment commences the following day in accordance with the administration schemes indicated. The compound of Example 1 is prepared in hydroxypropylcellulose, the suspension is then homogenised using an Ultra Turrax. The compound of Example 1 is administered by the IP route 30 to 60 minutes before the cytotoxic agent (0.2 ml in both cases).

The parameter measured is the survival time, allowing the calculation of T/C:

$$T/C = \frac{\text{median survival time of treated animals}}{\text{median survival time of control animals}} \times 100$$

The variation in weight is calculaed; it provides information on the toxicity of the treatment. The control groups comprise from 15 to 27 animals and the treated groups from 5 to 10 animals.

Six independent experiments were carried out. The assays were performed over 4 days in accordance with the scheme $D_{1-4}$ the tumour cells being implanted on $D_O$ and the reversing agent and the cytotoxic agnet being administered on $D_1$, $D_2$, $D_3$, and $D_4$.

The results obtained are set out in Table V in the form of overall results (T/C means and medians). Line P388 is very resistant, ADR alone not exhibiting any antitumour activity (T/C<120%)

The compound of Example 1, tested at from 50 to 200 mg/kg, does not possess any antitumour activity and is only moderately toxic at 200 mg/kg.

A modest activity is obtained with the compound of Example 1 at 50 and 100 mg/kg (120%<T/C<135%) and a good activity is obtained with 200 mg/kg of the compound of Example 1 and 2 mg/kg ADR (T/C =148.9%). In that case, the increase in activity as a result of the compound of Example 1 is 30.6%. Further, Table V shows that the activity is reproducible, the T/C means being very similar to the T/C medians when the number of independent experiments considered is four or six.

TABLE V

Line P388/ADR Cytotoxic agent ADR Scheme $D_{1-4}$ (QDX4, 1-4) Intraperitoneal administration, T/C means and medians

| Compounds | | $n^1$ | *T/C Extreme Values | *T/C Mean ± s.e.m. | *T/C Median |
|---|---|---|---|---|---|
| CONTROLS | | 6 | 100 | 100 | 100 |
| Example 1 | 50 mg/kg | 2 | 90–108.3 | 99.2 | 99.2 |
| " | 100 mg/kg | 6 | 85–100 | 91.7 ± 2.8 | 90 |
| " | 200 mg/kg | 4 | 80–88.9 | 83.5 ± 2.2 | 82.5 |
| ADR | 2 mg/kg | 2 | 116.7–120 | 118.3 | 118.3 |
| " | 4 mg/kg | 6 | 105–130 | 115.1 ± 3.9 | 112.5 |
| Example 1 + ADR | 50 mg/kg 2 mg/kg | 2 | 120–141.7 | 130.9 | 130.9 |
| + ADR | 4 mg/kg | 2 | 116.7–140 | 128.4 | 128.4 |
| Example 1 + ADR | 100 mg/kg 2 mg/kg | 2 | 116.7–140 | 128.4 | 128.4 |
| + ADR | 4 mg/kg | 6 | 120–150 | 134.2 ± 4.4 | 134.2 |
| Example 1 + ADR | 200 mg/kg 2 mg/kg | 4 | 140–155.6 | 148.9 ± 3.2 | 150 |

The results are expressed as T/C (%) which is the ratio of the median survival times of the treated animals/control animals
*T/C ≦ 85%: toxic
T/C ≧ 120%: Moderare activity
T/C ≧ 135%: Good activity (criterium for the selection of a compound).
T/C ≧ 175%: Significant activity
$n^1$ = number of independent experiments: number of values considered for calculating the T/C means and medians.

We claim:
1. A compound selected from those of formula I:

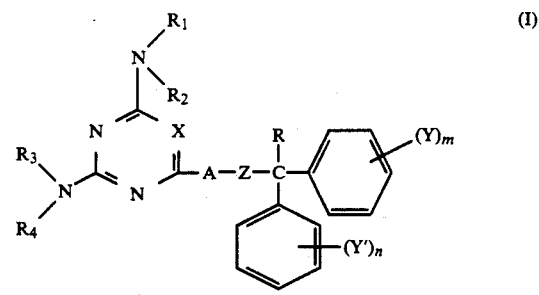

(I)

in which:
a) X represents nitrogen;
b) A represents the following group:

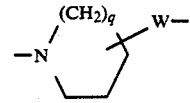

in which:

W represents oxygen, sulfur, or NR' in which R' represents hydrogen or alkyl or alkenyl each having up to 5 carbon atoms, inclusive and q is an integer from 1 to 3 inclusive;

c) $R_1$, $R_2$, $R_3$ and $R_4$, which are the same or different, each represents:

hydrogen, straight-chain or branched alkyl containing 1 to 6 carbon atoms inclusive which is optionally substituted by halogen, one or more hydroxy, or by —N($R_5$ $R_6$), in which $R_5$ and $R_6$, which are the same or different, each represents hydrogen or straight-chain, or branched alkyl containing 1 to 6 carbon atoms, inclusive, or alkenyl or alkynyl each containing from 2 to 6 inclusive carbon atoms;

or cycloalkyl containing from 3 to 6 ring carbon atoms inclusive;

d) Z represents straight-chain or branched hydrocarbon containing 1 to 5 carbon atoms inclusive;

e) R represents hydrogen, straight-chain or branched alkyl containing inclusive, 1 to 5 carbon atoms, straight-chain or branched alkenyl containing 2 to 5 carbon atoms inclusive, or phenyl optionally substituted by $(Y)_m$ or $(Y')_n$;

f) Y and Y', which are the same or different, each represents hydrogen or halogen, trifluoromethyl, or alkyl or alkoxy each containing, inclusive, 1 from 5 carbon atoms;

g) m and n, which are the same or different, each represents 1 or 2;

its diastereoisomers and enantiomers, as well as its addition salts with a physiologically tolerable acid.

2. A compound of claim 1, which is:

1-[4,6-bis(allylamino)-2-s-triazinyl]-4-[2,2-bis-(p-fluorophenyl)ethylamino]piperidine.

3. A compound of claim 1 which is:

1-[4,6-bis(allylamino)-2-s-triazinyl]-4-[2-(3,5-dimethoxyphenyl)-2-(2-methylphenyl)ethylamino]-piperidine.

4. A pharmaceutical composition useful in the suppression of cell resistance to anti-cancer or antitumour agents comprising as active ingredient an effective amount of a compound of claim 1 together with pharmaceutically-acceptable carrier.

5. A method for treating a living animal in need of the suppression of the resistance of tumour cells to anti-cancer agents, or the suppression of the resistance of parasites to anti-parasitic agents, comprising the step of administering to the said living animal body an amount of a compound of claim 1 which is effective for said suppression.

* * * * *

UNITED STATES PATENT AND TRADEMARK OFFICE
CERTIFICATE OF CORRECTION

PATENT NO. : 5,225,411

DATED : July 6, 1993

INVENTOR(S) : Gilbert Regnier, Alain Dhainaut, Ghanem Atassi, Alain Pierre, Stéphane Leonce Page 1 of 2

It is certified that error appears in the above-indentified patent and that said Letters Patent is hereby corrected as shown below:

Column 1, line 32; "NR," should read -- NR' --.
Column 2, approximately line 49; "presents" should read -- present --.
Column 7, approximately line 24; "(2,2di-" should read -- (2,2-di- --.
Column 8, approximately line 42; delete "5", first occurrence.
Column 8, approximately line 50; "(3,3di-" should read -- (3,3-di --.
Column 9, line 37; "35°" should read -- 135° --.
Column 10, line 25; "penioillin," should read -- penicillin --.
Column 11, approximately line 12; insert "B)" before "Evaluation".
Column 13, line 51; "calculaed;" should read --calculated;--.
Column 14, approximately line 37; "the med an" should read -- the median --.
Column 15, line 5; "3inclusive;" should read --3, inclusive;--. (PA 7-3-91, P. 1)
Column 15, line 16,17; "to 6 inclusive" should read -- to 6, inclusive, --.
Column 15, line 19; "atoms" should read -- atoms, -- .

Column 15, line 22; "atoms" should read --atoms, --.

Column 15, line 24; delete "inclusive," and insert "inclusive" at the end of line 24.
Column 15, line 26; "atoms inclusive" should read -- atoms, inclusive, --.

UNITED STATES PATENT AND TRADEMARK OFFICE
CERTIFICATE OF CORRECTION

PATENT NO. : 5,225,411
DATED : Jul. 6, 1993
INVENTOR(S) : Gilbert Regnier, Alain Dhainaut, Ghanem Atassi, Alain Pierre, Stéphane Leonce It is certified that error appears in the above-indentified patent and that said Letters Patent is hereby corrected as shown below:

Column 16, line 3, 4; "containing, inclusive, 1 from 5 carbon atoms;" should read -- containing 1 to 5 carbon atoms, inclusive; --.
Column 16, line 18; "with phar-" should read -- with a phar- --.
Column 16, line 25; "for said" should read -- for the said --.

Signed and Sealed this

Twenty-sixth Day of April, 1994

BRUCE LEHMAN

*Attest:*

*Attesting Officer*　　*Commissioner of Patents and Trademarks*